(12) United States Patent
Honma et al.

(10) Patent No.: US 8,617,596 B2
(45) Date of Patent: Dec. 31, 2013

(54) SUSTAINED-RELEASE TABLET PRODUCTION PROCESS

(75) Inventors: Takeshi Honma, Hamamatsu (JP); Kenji Furukawa, Hamamatsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 678 days.

(21) Appl. No.: 12/226,247

(22) PCT Filed: Apr. 10, 2007

(86) PCT No.: PCT/JP2007/057882
§ 371 (c)(1),
(2), (4) Date: Oct. 9, 2008

(87) PCT Pub. No.: WO2007/123021
PCT Pub. Date: Nov. 1, 2007

(65) Prior Publication Data
US 2009/0275672 A1 Nov. 5, 2009

(30) Foreign Application Priority Data
Apr. 12, 2006 (JP) .................................. 2006-109710

(51) Int. Cl.
*A61K 9/20* (2006.01)
*A61K 9/22* (2006.01)
*A61K 9/26* (2006.01)

(52) U.S. Cl.
USPC ........... 424/464; 424/465; 424/468; 424/469; 424/470

(58) Field of Classification Search
None
See application file for complete search history.

(56) References Cited

U.S. PATENT DOCUMENTS

| 4,259,314 | A | | 3/1981 | Lowey | |
|---|---|---|---|---|---|
| 4,704,285 | A | * | 11/1987 | Alderman | 424/468 |
| 5,009,895 | A | | 4/1991 | Lui | |
| 5,641,516 | A | | 6/1997 | Grabowski et al. | |
| 6,103,263 | A | | 8/2000 | Lee et al. | |
| 6,153,623 | A | | 11/2000 | Jans et al. | |
| 2006/0039974 | A1 | * | 2/2006 | Akiyama et al. | 424/468 |
| 2006/0127475 | A1 | | 6/2006 | Makino et al. | |
| 2007/0026065 | A1 | * | 2/2007 | Benke et al. | 424/468 |

FOREIGN PATENT DOCUMENTS

| EP | 0 923 934 | 6/1999 |
|---|---|---|
| JP | A-10-330269 | 12/1998 |
| JP | A-11-060476 | 3/1999 |

(Continued)

OTHER PUBLICATIONS

Nlsso HPC Data Sheet. Accessed online at http://www.nissoamerica.com/hpc/datasheet.pdf on Nov. 16, 2010.*

(Continued)

*Primary Examiner* — Carlos Azpuru
*Assistant Examiner* — Casey Hagopian
(74) *Attorney, Agent, or Firm* — Kenyon & Kenyon, LLP

(57) ABSTRACT

A process is provided for efficiently producing sustained-release tablets having superior sustained-release properties capable of inhibiting the initial elution of a drug and allowing the drug to be completely eluted after a prescribed amount of time has elapsed. A process for producing sustained-release tablets comprising: dry granulating a mixture composed of a hydroxyalkyl cellulose (A) having a viscosity of 1 to 50 mPa·s in a 2% by mass aqueous solution at 20° C., a hydroxyalkyl cellulose (B) having a viscosity of 100 mPa·s or more in a 2% by mass aqueous solution at 20° C., an active ingredient and an additive, and forming the resulting granules into tablets.

6 Claims, 2 Drawing Sheets

(56) References Cited

FOREIGN PATENT DOCUMENTS

| | | |
|---|---|---|
| JP | A-2002-322098 | 11/2002 |
| JP | 2003-171277 | 6/2003 |
| JP | 2004-217566 | 8/2004 |
| WO | 01/19349 | 3/2001 |
| WO | 03/084514 | 10/2003 |
| WO | 2005/102289 | 11/2005 |

OTHER PUBLICATIONS

Tanimura et al., "Direct Compaction of Poorly Compactable Pharmaceutical powders with Spray-dried HPC-L," J. Soc. Powder Technol., Japan, 43, 2006, pp. 648-652.*

Japanese Patent Office, International Search Report (translated) and Written Opinion dated Jul. 10, 2007, from related International Patent Application No. PCT/JP2007/057882.

European Search Report mailed Jan. 28, 2011, issued during the prosecution of EP 07741318.5, 5 pages.

Decision of Rejection issued in JP Appln. No. 2008-512067 on Aug. 14, 2012, English Abstract is provided, 5 pages.

Tousey, Michael D., et al., "Preventing and Fixing Weight and Hardness Defects: Strategies for Production Personnel", Sep. 2004, www.tabletscapsules.com, *Di Pharma Tech*, 5 pages.

Canadian Office Action issued for Canadian Application No. 2,648,667, mailed May 12, 2011, 3 pages.

* cited by examiner

SUSTAINED-RELEASE TABLET PRODUCTION PROCESS

This application is the national stage filing (35 U.S.C. §371) of PCT/JP2007/057882, filed on Apr. 10, 2007, which claims priority from Japanese Application No. JP 200-109710, filed on Apr. 12, 2006.

TECHNICAL FIELD

Priority is claimed on Japanese Patent Application No. 2006-109710, filed on Apr. 12, 2006, the content of which is incorporated herein by reference.

The present invention relates to a process for producing sustained-release tablets having superior sustained-release properties.

BACKGROUND ART

Sustained-release preparations containing pharmaceutical active ingredients are attracting attention as highly useful preparations capable of controlling blood concentrations of pharmacologically active ingredients and sustaining pharmacological effects. In the past, water-soluble polymers that form a gel by contact with water were used as such sustained-release preparations, and considerable research has been conducted on sustained-release preparations that sustain the release of a drug from a preparation (matrix type sustained-release preparations).

The following lists examples of such matrix type sustained-release preparations.
(a) Patent Document 1 describes a process for preparing a formulated preparation having a prolonged controlled action, comprising the steps of: mixing a dry support composed of 80 to 95% hydroxypropyl methyl cellulose (HPMC) and 20 to 5% hydroxypropyl cellulose (HPC), drying the support to a moisture content of 1% or less, forming a dry formulated preparation by mixing a therapeutically effective amount of a therapeutic agent into the dry support, and compressing the dry formulated preparation into a prescribed shape; wherein, the HPMC and the HPC have a viscosity within the range of 50 to 25000 centipoise (cps) at 20° C. for a 2% aqueous solution.
(b) Patent Document 2 describes a long-acting tablet comprising: fine particles of HPC, of which at least 50% by mass are able to pass through a 100 mesh screen, and HPMC having a hydroxypropoxy group content of 4 to 12%, methoxy group content of 19 to 30%, and viscosity in a 2% aqueous solution of 400 to 100,000 cps.
(c) Patent Document 3 describes a sustained-release preparation in the form of a cisapride oral sustained-release composition comprising: approximately 9% by mass of cisapride-(L)-tartrate, approximately 61% by mass of lactose, 5.5 to 18% HPMC, 5.5 to 18% HPC and approximately 6.5% by mass of a lubricant.
(d) Patent Document 4 describes a method for enhancing the gel strength of a preparation by containing HPMC and HPC in the preparation. According to the invention of a method for enhancing gel strength as described in this publication, it is described to the effect that gel strength is improved and a sustained-release preparation is obtained having superior sustained-release effects.
(e) Patent Document 5 describes an active substance-containing preparation in the form of a compressed tablet comprising a support material in the form of a mixture high viscosity and low viscosity hydroxypropyl methyl cellulose.

However, in each of the preparation described in the above-mentioned publications, and in the case of tablets and the like in particular, since there are cases in which the drug does not completely elute from inside the preparation or conversely the elution speed of drug from inside the preparation is too rapid, there are cases in which the desired sustained-release effects are unable to be obtained, this requiring further improvement of the sustained-release preparation (sustained-release tablets).

In addition, Patent Document 6 describes an active substance-containing preparation in the form of solid particles obtained by finely mixing an active substance with a support material in the form of a water-soluble melt composed of (a) 10 to 90% by mass of a water-soluble polymer A having a viscosity of 1000 to 12000 cps and (b) 10 to 90% by mass of a water-soluble polymer B having a viscosity of 1 to 500 cps, and forming the melt into particles. In addition, HPMC and HPC are indicated as examples of water-soluble polymer A while HPC is indicated as an example of water-soluble polymer B in this publication.

However, since the art described in this publication involves the formation of solid particles after having heated and melted an active substance, water-soluble polymer A and water-soluble polymer B, problems are encountered particularly in the case of using an active substance that is unstable (changes easily) with respect to heat.

[Patent Document 1] Japanese Examined Patent Application, Second Publication No. H4-4301
[Patent Document 2] Japanese Patent (Granted) Publication No. 2134343
[Patent Document 3] Japanese Patent (Granted) Publication No. 3182423
[Patent Document 4] Japanese Unexamined Patent Application, First Publication No. 2004-217566
[Patent Document 5] Japanese Unexamined Patent Application, First Publication No. H7-53364
[Patent Document 6] Japanese Unexamined Patent Application, First Publication No. H6-172160

DISCLOSURE OF THE INVENTION

Problems to be Solved by the Invention

With the foregoing in view, an object of the present invention is to provide a process for producing sustained-release tablets having superior sustained-release properties capable of inhibiting the initial elution of a drug and allowing the drug to be completely eluted after a prescribed amount of time has elapsed.

Means for Solving the Problems

As a result of conducting extensive studies to solve the above problems, the inventors of the present invention found that by dry granulating a mixture in which a plurality of types of hydroxypropyl cellulose having different viscosities in a 2% by mass aqueous solution at 20° C. and a vehicle are mixed at a prescribed ratio, and forming the resulting granules into tablets, a sustained-release preparation having superior sustained-release properties, in which initial elution of drug from inside the preparation can be inhibited and the drug completely elutes from inside the preparation after the passage of a desired amount of time, can be efficiently produced, thereby leading to completion of the present invention.

Thus, according to the present invention, a process for producing sustained-release tablets is provided as described in (1) to (9) below.

(1) A process for producing sustained-release tablets comprising: dry granulating a mixture composed of a hydroxyalkyl cellulose (A) having a viscosity of 1 to 50 mPa·s in a 2% by mass aqueous solution at 20° C., a hydroxyalkyl cellulose (B) having a viscosity of 100 mPa·s or more in a 2% by mass aqueous solution at 20° C., an active ingredient and an additive, and forming the resulting granules into tablets.

(2) A process for producing sustained-release tablets comprising directly forming into tablets a mixture composed of a hydroxyalkyl cellulose (A) having a viscosity of 1 to 50 mPa·s in a 2% by mass aqueous solution at 20° C., a hydroxyalkyl cellulose (B) having a viscosity of 100 mPa·s or more in a 2% by mass aqueous solution at 20° C., an active ingredient and an additive.

(3) The process for producing sustained-release tablets described in (1) or (2), wherein the hydroxyalkyl cellulose (A) is used at 20 to 70% by mass based on the entire mixture, the hydroxyalkyl cellulose (B) is used at 10 to 40% by mass based on the entire mixture, the active ingredient is used at 1 to 30% by mass based on the entire mixture, and the additive is used at 10 to 60% by mass based on the entire mixture.

(4) The process for producing sustained-release tablets described in any of (1) to (3), wherein a fine powder in which the proportion of fine particles having a particle diameter of 150 μm or less is 99% by mass or more is used for at least one of the hydroxyalkyl cellulose (A) or the hydroxyalkyl cellulose (B).

(5) The process for producing sustained-release tablets described in any of (1) to (4), wherein the total content of the hydroxyalkyl cellulose (A) and the hydroxyalkyl cellulose (B) is 40 to 80% by mass based on the entire mixture.

(6) The process for producing sustained-release tablets described in any of (1) to (5), wherein at least one of the hydroxyalkyl cellulose (A) and the hydroxyalkyl cellulose (B) is hydroxypropyl cellulose.

(7) The process for producing sustained-release tablets described in any of (1) to (6), wherein a mixture containing a fluidizing agent or lubricant at 0.01 to 1% by mass based on the mixture is used for the mixture.

(8) The process for producing sustained-release tablets described in any of (1) to (7), wherein the active ingredient is a cold medicine active ingredient.

(9) Sustained-release tablets produced according to the process for producing sustained-release tablets described in any of (1) to (8) above.

Effects of the Invention

According to the production process of the present invention, sustained-release tablets having superior sustained-release properties capable of inhibiting the initial elution of a drug from the inside a preparation and allowing the drug to completely elute from inside a preparation after prescribed amount of time has elapsed can be efficiently produced.

In the production process of the present invention, tablets having a high hardness can be produced in the case of using a fine powder in which the proportion of fine particles having a particle diameter of 150 μm or less is 99% by mass or more for hydroxyalkyl cellulose (A), and/or using fine particles in which the proportion of fine particles having a particle diameter of 150 μm or less is 99% by mass or more for hydroxyalkyl cellulose (B).

In addition, in the case of using a fluidizing agent or lubricant, the fluidity of a mixture composed of hydroxyalkyl cellulose (A), hydroxyalkyl cellulose (B), active ingredient and additive can be improved. Namely, fluidity can be secured that allows the mixture to be formed into tablets directly, and fluidity of the mixture before and after granulation treatment can be improved.

BEST MODE FOR CARRYING OUT THE INVENTION

Figure 1:
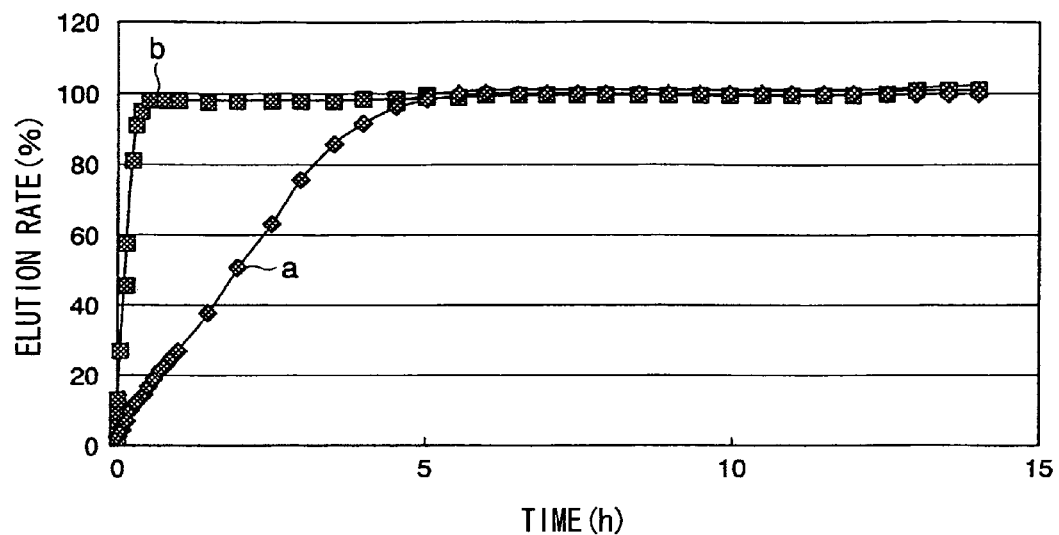
FIG. 1 is a graph showing changes in elution rate (%) of an active ingredient versus elapsed time in water of tablets obtained in Example 1 (a) and Comparative Example 1 (b).

The following provides a detailed explanation of the present invention.

The process for producing sustained-release tablets of the present invention comprises dry granulating a mixture containing a hydroxyalkyl cellulose (A) having a viscosity of 1 to 50 mPa·s in a 2% by mass aqueous solution at 20° C., a hydroxyalkyl cellulose (B) having a viscosity of 100 mPa·s or more in a 2% by mass aqueous solution at 20° C., an active ingredient and an additive, and either forming the resulting granules into tablets or forming the mixture directly into tablets.

(1) Hydroxyalkyl Cellulose

The hydroxyalkyl cellulose used in the present invention is a cellulose in which hydroxyl groups of the cellulose are hydroxyalkylated. Examples of hydroxyalkyl celluloses include hydroxyethyl cellulose, hydroxypropyl cellulose and hydroxypropyl methyl cellulose. One type of these hydroxyalkyl celluloses can be used alone, or two or more types can be used in combination.

Among these, the use of hydroxypropyl cellulose is particularly preferable in the present invention.

The hydroxyalkyl group content of the hydroxyalkyl cellulose used in the present invention is preferably 50 to 80%.

In addition, the use of a fine powder in which the proportion of fine particles having a particle diameter of 150 μm or less is 99% by mass or more is used for hydroxyalkyl cellulose (A), and/or a fine powder in which the proportion of fine particles having a particle diameter of 150 μm or less is 99% by mass or more is used for hydroxyalkyl cellulose (B) is preferable in terms of being able to produce tablets having a high hardness in the present invention.

The hydroxyalkyl cellulose used in the present invention can be prepared in accordance with a known method, such as by reacting an alkylene oxide such as ethylene oxide or propylene oxide with an alkaline cellulose. In addition, a commercially available product may also be used.

In the process for producing sustained-release tablets of the present invention, two or more types of hydroxyalkyl cellulose having different values for viscosity in a 2% by mass aqueous solution at 20° C. are used. The use of two or more types of hydroxyalkyl cellulose having different values for viscosity in a 2% by mass aqueous solution at 20° C. makes it possible to obtain sustained-release tablets having superior sustained-release properties capable of inhibiting initial elution of drug from inside a preparation, while also allowing the drug to completely elute from inside the preparation after a prescribed amount of time has elapsed.

Effects of containing two or more types of hydroxyalkyl cellulose having different values for viscosity in a 2% by mass aqueous solution at 20° C. in a preparation can be considered to be as described below.

Hydroxyalkyl cellulose has the property of dissolving in water by gelling upon contact with water. The rate at which hydroxyalkyl cellulose gels and dissolves in water is related to molecular weight. In general, hydroxyalkyl cellulose having a small molecular weight dissolves relatively rapidly in water, while hydroxyalkyl cellulose having a large molecular weight dissolves relatively slowly in water.

On the other hand, the viscosity of an aqueous solution of a water-soluble polymer is correlated with the molecular weight of the polymer, and hydroxyalkyl celluloses having different viscosities are hydroxyalkyl celluloses having different molecular weights. Namely, hydroxyalkyl celluloses having different values for viscosity in a 2% by mass aqueous solution at 20° C. can be said to be hydroxyalkyl celluloses having different dissolution rates in water.

Although there are no particular limitations on the production process of the present invention as long as two or more types of hydroxyalkyl celluloses are used that have different values for viscosity in a 2% by mass aqueous solution at 20° C., the use of hydroxyalkyl cellulose (A) having a viscosity in a 2% by mass aqueous solution at 20° C. of 1 to 50 mPa·s, preferably 3 to 20 mPa·s and particularly preferably 6 to 10 mPa·s, and hydroxyalkyl cellulose (B) having a viscosity in a 2% by mass aqueous solution at 20° C. of 100 mPa·s or more, preferably 500 to 10000 mPa·s and particularly preferably 1000 to 4000 mPa·s is preferable in terms of obtaining a preparation having even better sustained-release properties.

In the production process of the present invention, the total amount of hydroxyalkyl cellulose (A) and hydroxyalkyl cellulose (B) used is preferably 40 to 80% by mass based on the entire mixture. In addition, the content of hydroxyalkyl cellulose (A) is preferably 20 to 70% by mass based on the entire mixture, while the content of hydroxyalkyl cellulose (B) is preferably 10 to 40% by mass based on the entire mixture.

If the content of hydroxyalkyl cellulose (A) is less than 20% by mass, elution speed tends to decrease with time, while if in excess of 70% by mass, although there are no problems in terms of elution behavior, since the proportion of hydroxyalkyl cellulose (A) in the preparation increases, there is the risk of being unable to secure the required drug content.

If the content of hydroxyalkyl cellulose (B) is less than 10% by mass, there is the risk being unable to obtain sustained-released effects. On the other hand, if the content of hydroxyalkyl cellulose (B) exceeds 40% by mass, elution speed tends to decrease remarkably, resulting in the risk of eluted ingredients being unable to be completely eluted even if sufficient time is allotted therefore.

(2) Active Ingredient

There are no particular limitations on the active ingredient used in the present invention and a pharmaceutical active ingredient (for humans) such as a pharmaceutical or over-the-counter medicine; a veterinary drug active ingredient; an agricultural chemical active ingredient such as a fungicide, insecticide, herbicide, rodenticide, repellent or plant growth regulator; or an ingredient contained in foods such as an amino acid, peptide, nucleic acid or organic acid may be used. In addition, the active ingredient may be a poorly water-soluble active ingredient or hydrophilic or water-soluble active ingredient.

Examples of pharmaceutical active ingredients include active ingredients contained in drugs affecting the central nervous system such as hypnotic sedatives, antiepileptics, antipyretic analgesic anti-inflammatory agents, anti-Parkinson's agents or psychoneural agents; drugs affecting the peripheral nervous system such as skeletal muscle relaxants or autonomic neural agents; drugs affecting circulatory organs such as cardiotonics, antiarrhythmics, diuretics, antihypertensives or vasodilators; drugs affecting respiratory organs such as bronchodilators or antitussives; drugs affecting digestive organs such as gastric digestives, gastrointestinal regulatory agents or antacids; hormone preparations; antihistamines; vitamins; antiulcer agents; antibiotics; chemotherapy agents: or, herbal extracts.

In addition, an active ingredient for which long-acting effects are required is preferable for the active ingredient, examples of which include active ingredients contained in antiepileptics, active ingredients contained in anti-Parkinson's agents, cold medicine active ingredients and rhinitis active ingredients.

Examples of active ingredients contained in antiepileptics include phenacemide-based active ingredients, hydantoin-based active ingredients, oxazolidine-based active ingredients, barbiturate-based active ingredients, primidone-based active ingredients, aminobutyric acid-based active ingredients and sulfonamide-based active ingredients.

Examples of active ingredients contained in anti-Parkinson's agents include amantadine, biperiden, profenamine and levodopa.

Examples of cold medicine active ingredients include active ingredients contained in antipyretic analgesic anti-inflammatory agents, bronchodilators, antihistamines, antitussives, expectorants and antitussive expectorants (such as acetaminophen), vitamins or Chinese herbal medicines. Examples of rhinitis active ingredients include active ingredients contained in sympathomimetic agents, parasympathomimetic agents or antiallergic-anti-inflammatory agents.

These active ingredients can be used alone or in a combination of two or more types by suitably selecting from groups of the same or different series of drugs.

In addition, these active ingredients may also be used as an active ingredient in combination with caffeine (such as caffeine anhydrous, caffeine sodium benzoate, caffeine citrate or caffeine (monohydrate)), active ingredients contained in antacids or mucosal membrane protective agents (such as magnesium hydroxide, magnesium oxide, magnesium carbonate, magnesium silicate, aluminum potassium sulfate, synthetic aluminum silicate, synthetic hydrotalcite (e.g., Alcamac (trade name)), dihydroxyaluminum aminoacetate, dry aluminum hydroxide gel, magnesium aluminometasilicate, aluminum hydroxide-sodium bicarbonate coprecipitate (e.g., Kumulite (trade name)) or sucralfate), minerals or amino acids.

There are no particular limitations on the amount of active ingredient used, and although varying according to the type of active ingredient used and the like, the amount used is preferably 1 to 30% by mass and more preferably 1 to 10% by mass based on the overall mixture.

(3) Additives

The additive used in the present invention is an ingredient other than hydroxyalkyl celluloses (A) and (B) added during preparation of sustained-release tablets.

There are no particular limitations on the additives used in the present invention, and additives known in the prior art that are used in pharmaceutical preparations can be used. Examples of additives include vehicles including starches such as cornstarch, lactose, powdered sugar, granulated sugar, glucose, D-mannitol, light anhydrous silicic acid, talc, magnesium carbonate, calcium carbonate or direct compression lactose (DCL); binders such as sucrose, gelatin, powdered gum arabic, methyl cellulose, carmellose, crystalline cellulose-sodium carmellose, polyvinyl pyrrolidone, pullulan, dextrin, tragacanth, sodium alginate or alpha-starch; disintegration agents such as calcium carmellose, sodium crosscarmellose, crospovidone, lowly-substituted hydroxypropyl cellulose or starch; fluidizing agents and lubricants such as talc, wax, light anhydrous silicic acid, wet silicon dioxide, stearic acid, magnesium stearate or calcium stearate; surfactants including anionic surfactants such as sodium alkyl sulfate, and nonionic surfactants such as polyoxyethylene sorbitan fatty acid esters, polyoxyethylene fatty acid esters or polyoxyethylene castor oil derivatives; colorants such as tar dye, caramel, red iron oxide or titanium oxide; lipids; correctives such as sweeteners or fragrances; fillers; thickeners; adsorbents; preservatives such as antiseptics; buffers; wetting agents; antistatic agents; and, disintegration extenders.

The amount of additive used is normally within the range of 10 to 60% by mass based on the entire mixture.

In the present invention, in the case of desiring to obtain sustained-release tablets by forming tablets directly from the aforementioned mixture, it is preferable to use DCL for the vehicle ingredient and further use a fluidizing agent or lubricant in combination with the vehicle ingredient. In the case of combining the use of a fluidizing agent or lubricant, the fluidity of a mixture composed of hydroxyalkyl cellulose (A), hydroxyalkyl cellulose (B), an active ingredient and an additive can be improved. Namely, fluidity can be secured that allows the mixture to be formed directly into tablets, and fluidity of the mixture before and after granulation treatment can be improved.

The present invention is a process for producing sustained-release tablets comprising (i) dry granulating a mixture obtained by mixing the hydroxyalkyl cellulose (A), hydroxyalkyl cellulose (B), active ingredient and additive using a known granulating apparatus followed by forming the resulting granules into tablets, or (ii) forming the mixture directly into tablets.

The process of (i) above is suitable for forming tablets from a mixture containing an active ingredient that is unstable with respect to water or heat. Examples of granulation apparatuses used in the process of (i) above include a slug machine, chilsonator (manufactured by Hosokawa Micron Corp.), compacting machine, briquette machine or dry granulation apparatus (manufactured by Freund Corp.). The process of (ii) above is suitable for forming tablets from a mixture containing an active ingredient that is unstable with respect to water or heat in the same manner as the process of (i). In addition, this process is simpler since it eliminates the need for a granulation procedure.

There are no particular limitations on the tableting machine used to form tablets from granules or form tablets directly from the mixture as described above, and a known apparatus can be used. Examples of tableting machines that can be used include a rotary single tableting machine, rotary double tableting machine, two-stage (or three-stage) compression tableting machine, inclined roller tableting machine and high-speed automated tableting machine.

There are no particular limitations on the tableting pressure, and a pressure can be suitably selected from within the range of, for example, about 300 to 3000 kg/cm$^2$. There are no particular limitations on tablet size, and a tablet size of 20 to 3000 mg per capsule, for example, is preferable.

Sustained-release tablets obtained in the manner described above may be single-layer tablets or laminated tablets or core-shell tablets (compressed coated tablets) composed of a plurality of layers.

Sustained-release tablets obtained according to the production process of the present invention may be made to be in the form of coated tablets by forming a coating layer as necessary, or may be given improved ease of taking or stability by using a corrective and the like. Examples of coated tablets include sugar-coated tablets and film-coated tablets.

As a result of containing two or more types of hydroxyalkyl celluloses having different dissolution rates with respect to water, the sustained-release tablets obtained according to the production process of the present invention have superior sustained-release effects by being able to inhibit initial elution from inside a pharmaceutical preparation and allowing a drug to completely elute from inside a preparation after a desired amount of time has elapsed.

EXAMPLES

Although the following provides a more detailed explanation of the present invention based on examples thereof, the present invention is not limited to these examples.

Example 1 and Comparative Example 1)

The following ingredients (1) to (4) were mixed in the proportions indicated in Table 1 (parts by mass).
(1) Commercially available acetaminophen (API Corp.) was used for the active ingredient (to apply similarly hereinafter).
(2) DCL (trade name: Pharmatose DCL-21, DMV International Corp.) was used for the additive vehicle ingredient (to apply similarly hereinafter).
(3) Hydroxypropyl cellulose having a viscosity in a 2% by mass aqueous solution at 20° C. of 8.1 mPa·s (trade name: HPC-L (fine powder), Nippon Soda Co., Ltd., of which 99% or more has a particle diameter of 150 μm or less, to be abbreviated as "HPC-1") was used for hydroxyalkyl cellulose (A) (to be apply similarly hereinafter).
(4) In addition, hydroxypropyl cellulose having a viscosity in a 2% by mass aqueous solution at 20° C. of 1800 mPa·s (trade name: HPC-H (fine powder), Nippon Soda Co., Ltd., of which 99% or more has a particle diameter of 150 μm or less, to be abbreviated as "HPC-2") was used for hydroxyalkyl cellulose (B) having a viscosity in a 2% by mass aqueous solution at 20° C. of 100 mPa·s or more (to apply similarly hereinafter).

TABLE 1

|  | Example 1 | Comparative Example 1 |
| --- | --- | --- |
| Acetaminophen | 3 | 3 |
| DCL | 57 | 67 |
| HPC-1 | 30 | 30 |
| HPC-2 | 10 | — |

Next, 300 mg of the mixtures obtained above were formed directly into tablets at a pressure of 10 kN using a hydraulic press forming machine (RIKENPOWER, Riken Seiki Co., Ltd.) to respectively obtain straight, flat tablets having a diameter of 10 mm (thickness: about 3.1 mm).

The elapsed time in water and elution rate of the active ingredient (%) were measured for the tablets obtained in Example 1 and Comparative Example 1. The measurement results are shown in FIG. 1. In FIG. 1, "a" represents the measurement results for Example 1, while "b" represents the measurement results for Comparative Example 1. The tablets of Comparative Example 1 in which HPC-2 was not used did not demonstrate sustained-release properties.

Examples 2 and 3 and Comparative Examples 2 and 3

The following ingredients (1) to (4) were mixed in the proportions indicated in Table 2 (parts by mass).
(1) Active ingredient: Acetaminophen
(2) Vehicle: DCL
(3) HPC-1
(4) HPC-2

TABLE 2

|  | Example 2 | Example 3 | Comparative Example 2 | Comparative Example 3 |
|---|---|---|---|---|
| Acetaminophen | 3 | 3 | 3 | 3 |
| DCL | 47 | 27 | 67 | 47 |
| HPC-1 | 40 | 50 | — | — |
| HPC-2 | 10 | 20 | 30 | 50 |

Next, 300 mg of the mixtures obtained above were formed directly into tablets at a pressure of 10 kN using a hydraulic press forming machine (RIKENPOWER, Riken Seiki Co., Ltd.) to respectively obtain straight, flat tablets having a diameter of 10 mm (thickness: about 3.2 mm).

Figure 2:
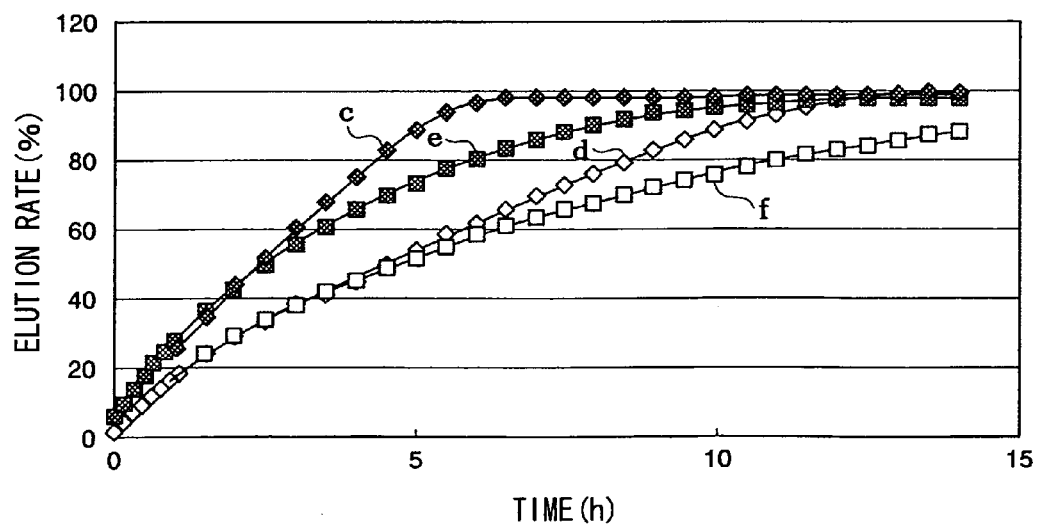
FIG. 2 is a graph showing changes in elution rate (%) of an active ingredient versus elapsed time in water of tablets obtained in Example 2 (c), Example 3 (d), Comparative Example 2 (e) and Comparative Example 3 (f).

The elapsed time in water and elution rate of the active ingredient (%) were measured for the tablets obtained in Examples 2 and 3 and Comparative Examples 2 and 3. The measurement results are shown in FIG. 2. In FIG. 2, "c" represents the measurement results for Example 2, "d" represents the measurement results for Example 3, "e" represents the measurement results for Comparative Example 2, and "f" represents the measurement results for Comparative Example 3.

On the basis of FIG. 2, the tablets of Examples 2 and 3 had sustained-release properties. However, the tablets of Comparative Examples 2 and 3 in which only HPC-2 was used were observed to demonstrate a decrease in elution speed with time in the latter stages of elution. In addition, the decreasing trend in elution speed was particularly remarkable in the case of Comparative Example 3, resulting in the risk of eluting ingredients being unable to be completely eluted even if sufficient time is allotted.

Examples 4 to 6

The following ingredients (1) to (4) were mixed in the proportions indicated in Table 3 (parts by mass).
(1) Active ingredient: Acetaminophen
(2) Vehicle: DCL
(3) HPC-1
(4) HPC-2

TABLE 3

|  | Example 4 | Example 5 | Example 6 |
|---|---|---|---|
| Acetaminophen | 3 | 3 | 3 |
| DCL | 17 | 7 | 7 |
| HPC-1 | 40 | 50 | 40 |
| HPC-2 | 40 | 40 | 50 |

Next, 300 mg of the mixtures obtained above were formed directly into tablets at a pressure of 10 kN using a hydraulic press forming machine (RIKENPOWER, Riken Seiki Co., Ltd.) to respectively obtain straight, flat tablets having a diameter of 10 mm (thickness: about 3.5 mm).

Figure 3:
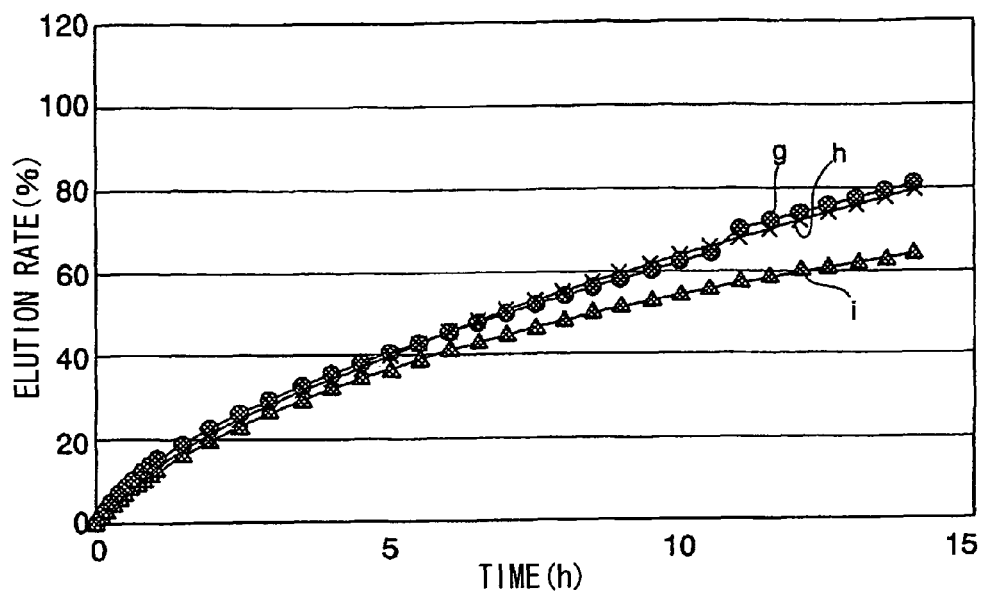
FIG. 3 is a graph showing changes in elution rate (%) of an active ingredient versus elapsed time in water of tablets obtained in Example 4 (g), Example 5 (h) and Example 6 (i).

The elapsed time in water and elution rate of the active ingredient (%) were measured for the tablets obtained in Examples 4 to 6. The measurement results are shown in FIG. 3. In FIG. 3, "g" represents the measurement results for Example 4, "h" represents the measurement results of Example 5, and "i" represents the measurement results for Example 6.

In the case of an HPC-1 content of 40% by mass and HPC-2 content of 40% by mass as in Example 4, there was hardly any change in elution behavior even if the HPC-1 content was changed from 40% by mass to 50% by mass (Example 5). However, when the HPC-2 content was changed from 40% by mass to 50% by mass (Example 6), the elution speed of the active ingredient tended to decrease during the latter half of elution. In this manner, although there is very little effect on elution behavior even if HPC-1 content exceeds 40% by mass, if HPC-2 content exceeds 40% by mass, the elution speed of the active ingredient decreases during the latter half of elution resulting in the risk of the active ingredient not being completely eluted.

Examples 7 and 8

The following ingredients (1) to (4) were mixed in the proportions indicated in Table 4 (parts by mass).
(1) Active ingredient: Acetaminophen
(2) Vehicle: DCL
(3) HPC-1
(4) HPC-2

TABLE 4

|  | Example 7 | Example 8 |
|---|---|---|
| Acetaminophen | 3 | 3 |
| DCL | 47 | 37 |
| HPC-1 | 30 | 40 |
| HPC-2 | 20 | 20 |

Next, 300 mg of the mixtures obtained above were formed directly into tablets at a pressure of 10 kN using a hydraulic press forming machine (RIKENPOWER, Riken Seiki Co., Ltd.) to respectively obtain straight, flat tablets having a diameter of 10 mm (thickness: about 3.2 mm).

Figure 4:
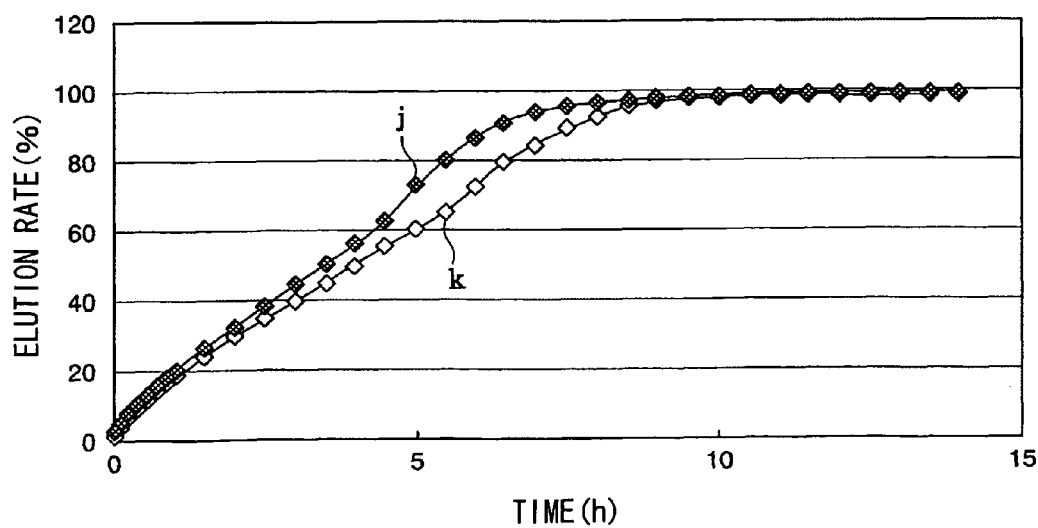
FIG. 4 is a graph showing changes in elution rate (%) of an active ingredient versus elapsed time in water of tablets obtained in Example 7 (j) and Example 8 (l).

The elapsed time in water and elution rate of the active ingredient (%) were measured for the tablets obtained in Examples 7 and 8. The measurement results are shown in FIG. 4. In FIG. 4, "j" represents the measurement results for Example 7, while "k" represents the measurement results for Example 8.

On the basis of FIG. 4, increases in elution speeds were observed for the tablets of Examples 7 and 8 starting after 4 to 6 hours had elapsed during the latter half of elution. This is thought to be the result of the temporary formation of a gel layer on the tablet surface followed by a portion of the gel layer separating from the tablets. Namely, the tablets of Examples 7 and 8 are sustained-release tablets having an accelerated elution capability.

Examples 9 and 10

The following ingredients (1) to (4) were mixed in the proportions indicated in Table 5 (parts by mass).
(1) Active ingredient: Acetaminophen
(2) Vehicle: DCL (3) HPC-1N (hydroxypropyl cellulose, trade name: HPC-L, Nippon Soda Co., Ltd., $D_{10}$=67.7 μm, $D_{50}$=170.3 μm, $D_{90}$=306.4 μm) HPC-1
(4) HPC-2N (hydroxypropyl cellulose, trade name: HPC-H, Nippon Soda Co., Ltd., $D_{10}$=67.7 μm, $D_{50}$=170.3 μm, $D_{90}$=306.4 μm) HPC-2

TABLE 5

|  | Example 9 | Example 10 |
| --- | --- | --- |
| Acetaminophen | 3 | 3 |
| DCL | 47 | 47 |
| HPC-1N | 30 | — |
| HPC-1 | — | 30 |
| HPC-2N | 20 | — |
| HPC-2 | — | 20 |

Next, 300 mg of the mixtures obtained above were formed directly into tablets at a pressure of 10 kN using a hydraulic press forming machine (RIKENPOWER, Riken Seiki Co., Ltd.) to respectively obtain straight, flat tablets having a diameter of 10 mm (thickness: about 3.2 mm).

Hardness was measured for the tablets obtained in Examples 9 and 10. Tablet hardness was measured using a tablet hardness meter (SCHLEUNIGER, Freund Corp.).

As a result, in contrast to the hardness of the capsules using HPC-1N and HPC-2N (Example 9) being 144 N, the hardness of the capsules using fine powder type HPC-1 and HPC-2 (Example 10) was 223 N. Thus, the use of fine powder type HPC-1 and HPC-2 was determined to allow the obtaining of tablets having high hardness.

Examples 11 and 12

The following ingredients (1) to (6) were mixed in the proportions indicated in Table 6 (parts by mass).
(1) Active ingredient: Acetaminophen
(2) Vehicle: DCL
(3) HPC-1
(4) HPC-2
(5) Light anhydrous silicic acid (trade name: Adsolider 101, Freund Corp.)
(6) Magnesium stearate (Mallinckrodt Inc.)

TABLE 6

|  | Example 11 | Example 12 |
| --- | --- | --- |
| Acetaminophen | 3.0 | 3.0 |
| DCL | 17.0 | 17.0 |
| HPC-1 | 60.0 | 60.0 |
| HPC-2 | 20.0 | 20.0 |
| Light anhydrous silicic acid | 0.5 | — |
| Magnesium stearate | 0.5 | — |

Next, apparent density and angle of repose were measured for the mixtures obtained above. The measurement results are shown in Table 7.

TABLE 7

|  | Example 11 | Example 12 |
| --- | --- | --- |
| Apparent Density (g/ml) | 0.38 | 0.35 |
| Angle of Repose (°) | 49.8 | 53.8 |

According to Table 7, the addition of light anhydrous silicic acid and magnesium stearate (Example 11) allowed the obtaining of a mixture having a larger apparent density and smaller angle of repose than in the case of not adding these substances (Example 12).

Next, 300 mg of the mixtures obtained above were formed into tablets at a pressure of 10 kN using a single tableting machine (FY-SS-7, Fuji Yakuhin Kikai Co., Ltd.) in an attempt to produce straight, flat tablets having a diameter of 10 mm (thickness: about 3.3 mm). As a result, although tablets were able to be easily obtained by direct compression for the mixture of Example 11, it was difficult to obtain tablets by direct compression for the mixture of Example 12.

Examples 13 and 14 and Comparative Example 4

The following ingredients (1) to (5) were mixed in the proportions indicated in Table 8 (parts by mass).
(1) Active ingredient: Acetaminophen
(2) Vehicle: DCL
(3) HPC-1
(4) HPC-2
(5) Magnesium stearate (Mallinckrodt Inc.)

TABLE 8

| Acetaminophen | 3.0 |
| --- | --- |
| DCL | 17.0 |
| HPC-1 | 60.0 |
| HPC-2 | 20.0 |
| Magnesium stearate | 0.5 |

Next, dry granulating was carried out on the mixture obtained above under the granulating conditions shown in Table 9 below using a dry granulator (TF-Mini Roller Compactor, Freund Corp.) (Examples 13 and 14) followed by measurement of apparent density and angle of repose. The measurement results are shown in Table 9.

TABLE 9

|  |  | Example 13 | Example 14 | Comparative Example 4 |
| --- | --- | --- | --- | --- |
| Granulating Conditions | Roller | 4 MPa, 8 rpm | | Mixed powder before granulation treatment |
| | Screw | 10 rpm | 20 rpm | |
| Apparent Density | | 0.42 | 0.48 | 0.35 |
| Angle of Repose (°) | | 48.0 | 46.1 | 53.8 |

As shown in Table 9, the mixtures of Examples 13 and 14, which underwent dry granulation following the addition of a fluidizing agent/lubricant in the form of magnesium stearate demonstrated larger apparent densities and smaller angles of repose than the mixed powder prior to granulation (Comparative Example 4).

Moreover, straight, flat tablets having a diameter of 10 mm (thickness: about 3.3 mm) were able to be obtained by tableting 300 mg of the granules of Examples 13 and 14 using a rotary tableting machine (HT-P15A-III, Hata Iron Works Co., Ltd.) at a pressure 10 kN.

The invention claimed is:
1. A process for producing sustained-release tablets comprising:
  dry granulating a mixture composed of a hydroxyalkyl cellulose (A) having a viscosity of 1 to 50 mPa*s in a 2% by mass aqueous solution at 20° C., a hydroxyalkyl cellulose (B) having a viscosity of 100 mPa*s or more in a 2% by mass aqueous solution at 20° C., an active ingredient and an additive, and forming the resulting granules into tablets, wherein a fine powder in which the proportion of fine particles having a particle diameter of 150 μm or less is 99% by mass or more is used for both the hydroxyalkyl cellulose (A) and the hydroxyalkyl cellulose (B), wherein the hydroxyalkyl cellulose (A) is used at 20 to 60% by mass based on the entire mixture, the hydroxyalkyl cellulose (B) is used at 10 to 40% by mass based on the entire mixture, the active ingredient is used at 1 to 30% by mass based on the entire mixture, and the additive is used at 10 to 60% by mass based on the entire mixture, and wherein the total content of the hydroxyalkyl cellulose (A) and the hydroxyalkyl cellulose (B) is 40 to 70% by mass based on the entire mixture.

2. A process for producing sustained-release tablets comprising: directly forming into tablets a mixture composed of a hydroxyalkyl cellulose (A) having a viscosity of 1 to 50 mPa*s in a 2% by mass aqueous solution at 20° C., a hydroxyalkyl cellulose (B) having a viscosity of 100 mPa*s or more in a 2% by mass aqueous solution at 20° C., an active ingredient and an additive, wherein a fine powder in which the proportion of fine particles having a particle diameter of 150 μm or less is 99% by mass or more is used for both the hydroxyalkyl cellulose (A) and the hydroxyalkyl cellulose (B), wherein the hydroxyalkyl cellulose (A) is used at 20 to 60% by mass based on the entire mixture, the hydroxyalkyl cellulose (B) is used at 10 to 40% by mass based on the entire mixture, the active ingredient is used at 1 to 30% by mass based on the entire mixture, and the additive is used at 10 to 60% by mass based on the entire mixture, and wherein the total content of the hydroxyalkyl cellulose (A) and the hydroxyalkyl cellulose (B) is 40 to 70% by mass based on the entire mixture.

3. The process for producing sustained-release tablets according to claim 1 or 2, wherein at least one of the hydroxyalkyl cellulose (A) and the hydroxyalkyl cellulose (B) is hydroxypropyl cellulose.

4. The process for producing sustained-release tablets according to claim 1 or 2, wherein said mixture contains a fluidizing agent or lubricant which is part of said additive, at 0.01 to 1% by mass based on the mixture.

5. The process for producing sustained-release tablets according to claim 1 or 2, wherein the active ingredient is a cold medicine active ingredient.

6. Sustained-release tablets produced according to the process for producing sustained-release tablets according to claim 1 or 2.

* * * * *